United States Patent [19]

Adachi et al.

[11] Patent Number: 5,073,048
[45] Date of Patent: Dec. 17, 1991

[54] OPTICAL FIBER BUNDLE

[75] Inventors: Rensuke Adachi; Shizuharu Miura; Hiroshi Sano, all of Tokyo, Japan

[73] Assignee: Asahi Kogaku Kogyo K.K., Tokyo, Japan

[21] Appl. No.: 215,665

[22] Filed: Jul. 6, 1988

[30] Foreign Application Priority Data

Jul. 6, 1987 [JP] Japan .................................. 62-169386
Jul. 24, 1987 [JP] Japan .................................. 62-185693
Jan. 28, 1988 [JP] Japan ............................ 63-10189[U]

[51] Int. Cl.$^5$ ................................................ G02B 6/04
[52] U.S. Cl. ...................................... 385/115; 385/116; 385/117
[58] Field of Search ............... 350/96.24, 96.25, 96.26, 350/96.23

[56] References Cited

U.S. PATENT DOCUMENTS

| 3,624,816 | 11/1971 | Strack | 350/96.24 |
| 4,213,672 | 7/1980 | Aulich et al. | 350/96.23 |
| 4,523,806 | 6/1984 | Kojima et al. | 350/96.24 |
| 4,753,224 | 6/1988 | Tojo | 350/96.25 X |
| 4,784,464 | 11/1988 | Ouchi | 350/96.24 X |
| 4,786,137 | 11/1988 | Cornelison et al. | 350/96.23 |

Primary Examiner—John D. Lee
Assistant Examiner—Phan T. Heartney
Attorney, Agent, or Firm—Sughrue, Mion, Zinn Macpeak & Seas

[57] ABSTRACT

An optical fiber bundle for an endoscope or the like which can be subjected to cyclic bending at a small radius of curvature without causing fiber breakage. The fiber bundle includes a plurality of optical fibers bound at both ends but with individual fibers being freely movable inside the middle portion of the bundle, which is covered by a flexible tube. A gelling fluid coating the fibers is filled in the flexible tube.

21 Claims, 2 Drawing Sheets

OPTICAL FIBER BUNDLE

BACKGROUND OF THE INVENTION

The present invention relates to an optical fiber bundle.

A bundle of optical fibers having a small diameter of about 0.01 to 0.02 mm is mainly used in an endoscope used for examining the insides of organs such as the stomach, intestines and bronchial tubes. As the tip of the endoscope is guided in a desired direction, the optical fibers are subjected to cyclic bending at small radii of curvature and become highly prone to breakage. Therefore, it has been long desired in the fiber optics industry to develop a fiber bundle that will not easily break upon repeated microbending.

The practice conventionally adopted to meet this need is to apply a coating of an antifriction agent such as a molybdenum disulfide powder or an oil on all parts of the optical fibers, except at both ends where the fibers are bound together, so that the individual fibers will slide smoothly against one another. The fibers treated in this manner are covered with a flexible tube.

Optical fibers themselves neither expand nor contract, and hence when an optical fiber bundle is bent at a small radius of curvature, all fibers, in an attempt at converging in the neutral plane, will spread laterally in the flexible tube, causing the latter to deform into a flat shape resembling a cobra's hood, as shown in FIG. 3. Being coated with an antifriction agent to provide better slippage between individual optical fibers, the prior art optical fiber bundle permits all fibers to move freely and individually. Therefore, if the bundle is subjected to repeated deformation on account of cyclic bending at small radii of curvature, the fibers will become twisted or entangled, bringing them out of alignment and breaking at portions where misalignment occurs.

If optical fibers in an image transmitting fiber bundle break, a black spot will appear on the viewing screen, making accurate diagnosis difficult. Moreover, if fiber breakage occurs in an illuminating fiber bundle, the quantity of illuminating light is decreased, reducing the brightness of the screen. In this case too, diagnosis becomes more difficult.

Therefore, if the prior art optical fiber bundle is to be employed in an endoscope, the inner space of the flexible pipe attached to the endoscope and which is to be inserted into an organ of interest is made large enough to ensure that the fiber bundle will not break upon compression by a forceps channel, air/water tubes, or any other element that is to be assembled in the flexible pipe. However, this prevents the insertion of many elements or thick elements into the flexible pipe, thereby putting considerable limits on the capabilities of the endoscope.

An object, therefore, of the present invention is to provide a durable optical fiber bundle that is free from the aforementioned problems of the prior art and which can be subjected to cyclic bending at a small radius of curvature without causing fiber breakage.

Further, the present invention relates to an improvement of the flexible tube serving as an outer sheath for the optical fiber bundle.

Conventional image transmitting or illuminating optical fiber bundles for use in endoscope are commonly sheathed with a flexible tube made of silicone rubber before they are slipped into the inserting portion of an endoscope. However, if the optical fiber bundle is cyclically bent in such areas at the curving area of the inserting portion, the fiber bundle is compressed by the forceps channel and other elements in the inserting portion of the endoscope, which can be a cause of damage to the optical fibers in the bundle. In order to increase the durability of the optical fibers, it has been proposed that the flexible tube of silicone rubber be reinforced with an outer tube. (See, for example, Japanese Unexamined Published Utility Model Application No. 74110/1985).

However, a dual sheath on the optical fiber bundle not only increases the production cost of the fiber bundle, but it also increases the diameter of the fiber bundle and the forceps channel and other elements to be incorporated in the inserting portion of an endoscope must be made thinner by a corresponding amount, leading to a reduction of the capabilities of the endoscope.

Another object of the present invention therefore is to eliminate the drawbacks of the prior art and to provide a durable optical fiber bundle for an endoscope that is sheathed with a single outer tube and which yet can be bent cyclically without causing breakage of the optical fibers.

SUMMARY OF THE INVENTION

The present invention attains the above and other objects by an optical fiber bundle which is generally of such a type that a number of optical fibers are bound at both ends, with the individual fibers being rendered freely movable and covered with a flexible tube in the middle portion between the two ends. The fiber bundle of the present invention is characterized in that the optical fibers in the flexible tube are coated with a gelling fluid.

Those portions of the optical fibers which are coated with a gelling fluid retain high flexibility and yet are bound together by that fluid more loosely than when they are coated with an adhesive but more tightly than when they are coated with a molybdenum disulfide powder or an oil. Therefore, when this portion of the fiber bundle is bent at a small radius of curvature, several hundred or more than a thousand fibers will move not separately but en masse without becoming entangled or coming out of alignment.

Further, the present invention attains the above and other objects by an optical fiber bundle which is generally of such type that a number of optical fibers are bundled at both ends, with the individual fibers being rendered freely movable and covered with a flexible tube in the middle portion between the two ends. The fiber optical fibers in the flexible tube are coated with a gelling fluid together with a gelation retarding material, the gelling fluid being capable of gelation upon heating or standing at normal temperatures.

The gelation retarding material controls the degree of gelation in such a way that the overall fiber bundle will maintain flexibility and assume a smooth shape even if it is bent at a small radius of curvature.

The present invention attains the above objects by an optical fiber bundle for an endoscope comprising a number of optical fibers that are bound at both ends, with the individual fibers being rendered freely movable and covered with a flexible tube of a polyurethane resin in the middle portion between the two ends, thereby forming a bundle of optical fibers which is slipped into the inserting portion of the endoscope.

In a preferred embodiment, the optical fibers in the flexible tube made of a polyurethane resin may be coated with liquid silicone that gels upon heating or standing at normal temperatures.

The polyurethane resin tube has high mechanical strength so that the optical fibers in the bundle will not be easily damaged even if it is compressed by the forceps channel or other elements in the inserting portion of an endoscope. As a further advantage, the polyurethane resin tube has an excellent resistance to chemical corrosion and is not attacked by liquid silicone or other chemicals with which it is to be filled.

DESCRIPTION OF THE PREFERRED EMBODIMENTS

Figure 1:
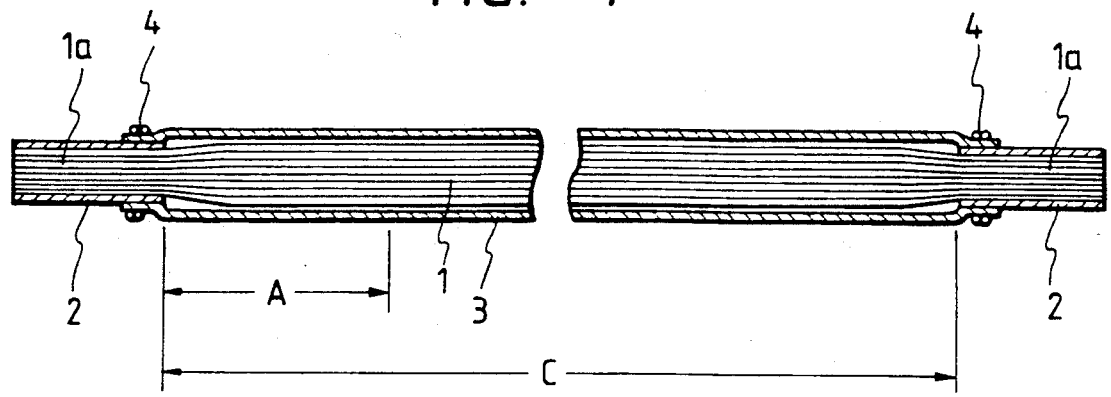
FIG. 1 is a longitudinal sectional view of an optical fiber bundle according to a first embodiment of the present invention.

FIG. 1 shows a first embodiment of the present invention applied to an image transmitting optical fiber bundle. In FIG. 1, reference numeral 1 denotes a fiber bundle composed of several tens of thousand optical fibers typically having a diameter of 0.01 mm. The individual fibers are arranged in such a way that the fibers at one end 1a are in alignment with those at the other end 1a, and are joined to a tubular metal cap 2 at each end 1a. The fibers are made freely movable in all parts of the bundle except at both ends 1a, and they are covered with a flexible tube 3 which is typically made of a silicone resin. Both ends of the flexible tube 3 are joined to the circumference of the cap 2 and fixed in position by being tightened with a thread 4.

In that part of the fiber bundle which is in the neighborhood of one end (the area indicated by A in FIG. 1), a gelling fluid is applied to the individual fibers which are then placed in the flexible tube 3. A suitable gelling fluid to be applied to the fibers is liquid silicone that will gel either upon heating or upon standing at normal temperature.

An optical fiber bundle incorporated in an endoscope is bent at a small radius of curvature only in the forwardmost area of the portion inserted into the organ of interest. Therefore, the durability of the fiber bundle will be greatly improved if a gelling fluid is coated at least on that part of the fiber bundle which is close to one end of the bundle, as in the case of the first embodiment described above.

Figure 2:
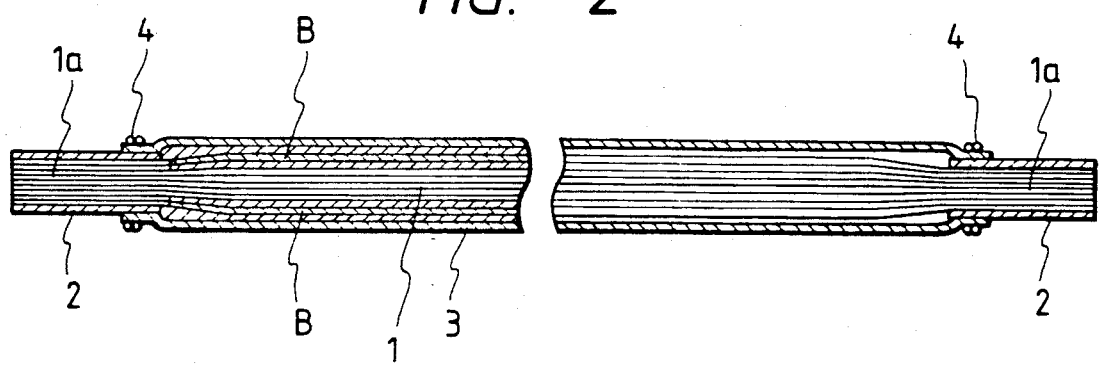
FIG. 2 shows a longitudinal section of an optical fiber bundle according to a second embodiment of the present invention.
Figure 3:
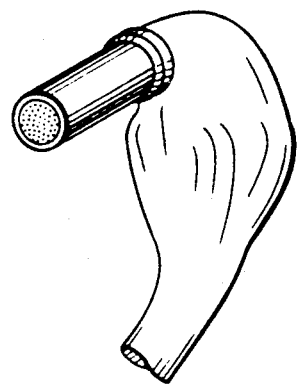
FIG. 3 is a perspective view of an optical fiber bundle bent at a small radius of curvature.

FIG. 2 shows a second embodiment of the present invention in which a gelling fluid is coated only on the optical fibers in the marginal area of the bundle (as indicated by the hatched area B in FIG. 2). When an optical fiber bundle is bent at a small radius of curvature, the fibers in the marginal area will move greatly but those in the central portion always remain in the neutral plane and scarcely move. In other words, no fiber misalignment will be introduced into the fiber bundle even if the fibers in the central portion are not coated with a gelling fluid. Therefore, the durability of the fiber bundle can also be improved significantly by coating a gelling fluid only on the optical fibers in the marginal portion of the bundle.

Although not shown, a gelling fluid may be coated on all parts of the optical fibers in the bundle except at the two ends where they are bound together. Needless to say, this embodiment is also included within the scope of the present invention.

The concept of the present invention may be applied to either an image transmitting optical fiber bundle or an illuminating optical fiber bundle.

In accordance with the present invention, a selected portion of the optical fibers in a bundle is coated with a gelling fluid. When this portion of the fiber bundle is bent at a small radius of curvature, several hundred or more than a thousand fibers will move as a unit, rather than moving separately to become entangled or come out of alignment. Therefore, the optical fiber bundle of the present invention exhibits excellent durability and can be cyclically bent at a small radius of curvature without damaging the optical fibers.

Because of this improved durability, the inner space of the flexible pipe attached to an endoscope and which is to be inserted into an organ of interest need not be made unduly large, thus avoiding damage to the optical fibers. As a result, great benefits can be attained by making the flexible pipe thin enough to minimize the pain felt by the patient, or by inserting more (or thicker) elements into a flexible pipe of the same diameter so as to realize greater improvements in the capabilities of the endoscope.

A third embodiment of the invention will now be described. In the third embodiment, the optical fiber bundle 1 is coated with a fine molybdenum disulfide powder over the entire length (i.e., the area indicated by C in FIG. 1), and thereafter accommodated in the flexible tube 3. The fine molybdenum disulfide powder serves not only as a lubricant or antifriction agent, but also as a gelation retarding material that retards the gelation of the liquid silicone gelling liquid to be described below. Molybdenum disulfide may be replaced by other suitable materials such as boron nitride.

In that part of the fiber bundle near one end (the area indicated by A in FIG. 1), liquid silicone that gels either upon heating or upon standing at normal room temperatures is applied to the individual fibers, which are then placed in the flexible tube 3. The liquid silicone is a dimethyl silicone based liquid that contains a platinum catalyst or some other component necessary to effect crosslinking. The catalytic action of this compound is retarded in the presence of sulfur, nitrogen, or some other element. Therefore, the gelation of the liquid silicone is retarded if it is present together with a sulfur compound (e.g., molybdenum disulfide) or a nitride compound (e.g., boron nitride).

In the embodiment being discussed, the optical fibers thus coated with a gelation retarding material and liquid silicone are subjected to a gelling treatment by heating or standing at normal temperatures.

In this embodiment, the optical fibers are bound by the partly gelled liquid silicone more loosely than when they are coated with an adhesive, but more tightly than when they are coated with a molydenum disulfide powder or an oil. When this portion of the fiber bundle is bent at a small radius of curvature, several hundred or more than a thousand fibers will move as a unit. Therefore, the fibers will not move separately to become entangled or come out alignment. In addition, the gelation retarding material controls the degree of gelation of the liquid silicone in such a way that the overall fiber bundle will maintain flexibility and assume a smooth shape even if it is bent at a small radius of curvature. Since the liquid silicone gels to some extent, it has limited flowability and will not flow out of the fiber bundle by permeating through the uncoated areas.

An optical fiber bundle incorporated in an endoscope is bent at a small radius of curvature only in the forwardmost of the portion to be inserted into an organ of interest. Therefore, the durability of the fiber bundle will be greatly improved if a gelling liquid silicone is coated at least on that part of the fiber bundle which is near one end of the bundle as in the case of the third embodiment described above.

In a fourth embodiment of the present invention, a fluid that gels upon heating or standing at normal temperatures is coated only on the optical fibers in the marginal portion of the bundle (as indicated by the hatched area B in FIG. 2). The gelation retarding material is coated on all part of the fibers. When an optical fiber is bent at a small radius of curvature, the fibers in the marginal area will move greatly while those in the central portion always remain in the neutral plane and will scarcely move. In other words, no fiber misalignment will be introduced into the fiber bundle even if the fibers in the central portion are not coated with a gelling fluid. Therefore, the durability of the fiber bundle can also be improved significantly by coating a gelling fluid only on the optical fibers in the marginal portion of the bundle.

In accordance with the present invention, a selected portion of the optical fibers in a bundle is coated with a fluid that gels upon heating or standing at normal temperatures. When this portion of the fiber bundle is bent at a small radius of curvature, several hundred or more than a thousand fibers will move as a unit, rather than moving separately to become entangled or come out of alignment. In addition, a gelation retarding material is employed to control the degree of gelation of the gelling fluid in such a way that the overall optical fiber bundle will maintain flexibility. Therefore, the optical fiber bundle of the present invention exhibits excellent durability and can be cyclically bent at a small radius or curvature without damaging the optical fibers.

Further embodiments of the invention will be described with reference to FIGS. 4 and 5. In these embodiments, the flexible tube 3 is made of a polyurethane resin.

The flexible tube 3 made of polyurethane resin has superior characteristics such as high toughness and high resistance to wear and chemical corrosion. Compared with a silicone rubber tube, the polyurethane resin tube is particularly high in mechanical strength. The silicone rubber tube will swell somewhat when it is filled with liquid silicone as in the embodiments described above, but not such swelling as occurs with a polyurethane resin tube.

Figure 4:
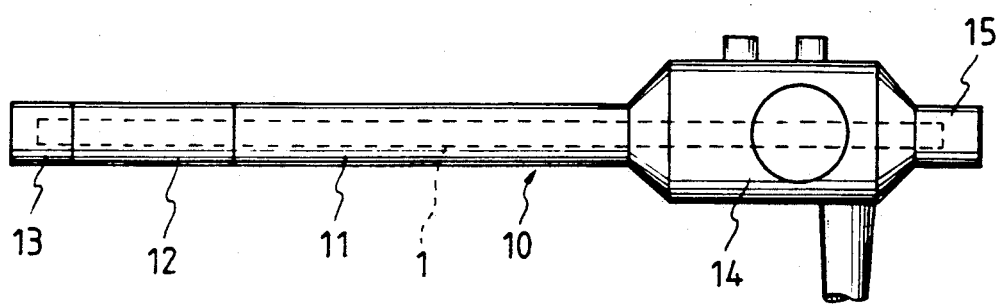
FIG. 4 is a general side view of an endoscope in which an optical fiber bundle is assembled.

FIG. 4 shows the optical fiber bundle 1 which is assembled in an endoscope. Indicated by 10 is the inserting portion of the endoscope which is composed of a flexible pipe portion 11 of known construction, a curving portion 12 that is freely bendable by manipulation at a remote area, and probe 13 connected to the tip of the curving portion 12. The base end of the flexible pipe portion 11 is connected to a manipulating unit 14. The optical fiber bundle 1 is slipped into the inserting portion 10 over its entire length. One end of the fiber bundle 1 is connected to the probe 13 and the other end is connected to an eyepiece 15 attached to the end of the manipulating unit 14.

Figure 5:
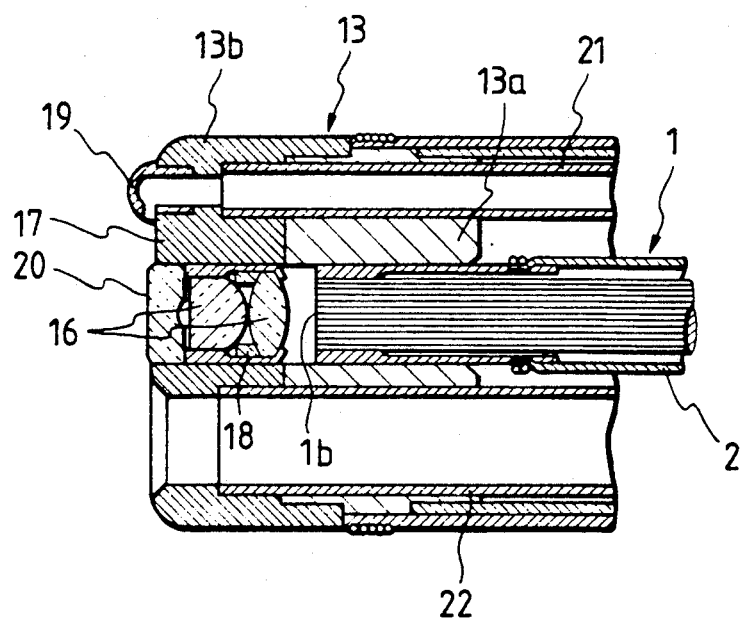
FIG. 5 is an enlarged sectional view of the top of the endoscope.

FIG. 5 shows the area in the vicinity of the probe 13 to which one end of the optical fiber bundle 1 is connected. Indicated by 13a is a metallic portion serving to ensure the strength of the probe, and 13 is a synthetic resin portion that ensures electrical insulation from the environment. Objective lenses 16 that are separated by a spacer 18 are incorporated in the probe 13 via a lens barrel 17, and an end 1b of the optical fiber bundle into which rays of light are applied is positioned at the image focusing point of the objective lens system 16. Indicated by 19 is a nozzle that is open toward the surface of a viewing window 20. This nozzle is connected to an air/water tube 21. Shown by 22 is a forceps channel that is typically formed of a polytetrafluoroethylene tube.

When the curving portion 12 or flexible pipe portion 11 in the embodiment described above is bent, the optical fiber bundle 1 is compressed by the forceps channel 22 and other elements in the inserting portion 10. However, the flexible polyurethane resin tube 3 with which the optical fiber bundle 1 is sheathed is tough and offers sufficient mechanical strength to prevent the optical fibers from breaking. Furthermore, as already mentioned, the polyurethane made flexible tube 3 will not swell in the presence of liquid silicone or other chemicals, and its thickness and strength remain unchanged for a sufficiently long period to afford intended protection of the optical fibers.

It should also be mentioned that besides liquid silicone, the flexible tube 3 within which the optical fiber bundle is accommodated may be filled with a fine molybdenum disulfide powder, boron nitride or other suitable material. It should be understood that the concept of the present invention is applicable to an illuminating optical fiber bundle.

The optical fiber bundle of the present invention for use in an endoscope employs a flexible tube made of a polyurethane resin as an outer sheath, which enables the fiber bundle to be compressed by other elements in the inserting portion of the endoscope without causing potential damage to the optical fibers. Therefore, the optical fiber bundle of the present invention exhibits satisfactory durability even if it is not covered with a dual sheath. Other advantages that result from the use of a single tube as the outer sheath of the optical fiber bundle are that the capabilities of the endoscope do not deteriorate and that is can be manufactured at a lower cost. It is apparent that the present invention is not limited to the endoscope but may be applicable to any kind of observation optical systems.

We claim:

1. An optical fiber bundle comprising:
 a plurality of optical fibers bound at both ends, individual fibers being freely movable;
 a flexible tube covering a middle portion between the two ends; and
 a gelling fluid applied to the optical fibers in the flexible tube wherein said gelling fluid gels upon being heated or standing at normal room temperatures.

2. The optical fiber bundle according to claim 1, in which the optical fibers are bound at both ends in such a way that the fibers at one end are in alignment with those at the other end.

3. The optical fiber bundle according to claim 1, wherein said gelling fluid is liquid silicone.

4. The optical fiber bundle according to claim 1, wherein said gelling fluid is applied to said optical fibers at least in an area near one end of said fiber bundle.

5. The optical fiber bundle according to claim 1, wherein said gelling fluid is applied only to optical fibers in a marginal portion of said fiber bundle.

6. The optical fiber bundle according to claim 1, wherein said gelling fluid is applied to all optical fibers except at both ends where they are bound together.

7. An optical fiber bundle for an endoscope comprising: a plurality of optical fibers bound at both ends, individual fibers being rendered freely movable; and a flexible tube of a polyurethane resin in a middle portion between the two ends of said optical fibers, thereby forming a bundle of optical fibers which can be slipped into an inserting portion of the endoscope, without a dual case structure, wherein said optical fibers in said flexible tube of polyurethane resin are coated with a liquid silicone that gels upon heating or standing at normal temperatures.

8. An optical fiber bundle comprising: a plurality of optical fibers bound at both ends, individual fibers being rendered freely movable; a flexible tube covering a middle portion between the two ends; and a gelling fluid and a gelation retarding material applied to said fibers in the flexible tube.

9. The optical fiber bundle according to claim 8, in which the optical fibers are bound at both ends in such a way that the fibers at one end are in alignment with those at the other end.

10. The optical fiber bundle according to claim 8, wherein said fluid is liquid silicone that gels upon heating or upon standing at normal room temperatures.

11. The optical fiber bundle according to claim 8, wherein said fluid is applied to said optical fibers on at least one end of said fiber bundle.

12. The optical fiber bundle according to claim 8, wherein said gelling fluid is applied to all optical fibers except at both ends where they are bound together.

13. The optical fiber bundle according to claim 8, wherein said gelation retarding material is a sulfur compound.

14. The optical fiber bundle according to claim 13, wherein said gelation retarding material is molybdenum disulfide.

15. The optical fiber bundle according to claim 8, wherein said gelation retarding material is a nitride compound.

16. The optical fiber bundle according to claim 15, wherein said gelation retarding material is boron nitride.

17. An optical fiber bundle for an endoscope comprising: a plurality of optical fibers bound at both ends, individual fibers being rendered freely movable; and a flexible tube of a polyurethane resin in a meddle portion between the two ends of said optical fibers, thereby forming a bundle of optical fibers which can be slipped into an inserting portion of the endoscope, without a dual case structure, wherein a liquid silicon and a gelation retarding material are applied to said optical fibers in said flexible tube of polyurethane resin.

18. A method of producing an optical fiber bundle, comprising the steps of:
binding a plurality of optical fibers at both ends; and
applying gelling fluid which gels upon being heated or standing at normal room temperatures to the individual optical fibers which are rendered freely movable.

19. The method of claim 18, further comprising inserting said fibers into a flexible tube.

20. A method of producing an optical fiber bundle, comprising the steps of:
binding a plurality of optical fibers at both ends; and
applying gelling fluid and gellation retarding material to the individual optical fibers which are rendered freely movable.

21. The method of claim 20, further comprising inserting said fibers into a flexible tube.

* * * * *

UNITED STATES PATENT AND TRADEMARK OFFICE
CERTIFICATE OF CORRECTION

PATENT NO.   : 5,073,048
DATED        : December 17, 1991
INVENTOR(S)  : Rensuke Adachi et al It is certified that error(s) appears in the above-identified patent and that said Letters Patent is hereby corrected as shown below:

Title page, left column, line [75], after "Sano", insert:

--, Shinichi Matsuno--.

Signed and Sealed this

Thirtieth Day of May, 1995

BRUCE LEHMAN

Attest:

*Attesting Officer*       *Commissioner of Patents and Trademarks*